United States Patent [19]

Robin

[11] 4,412,073
[45] Oct. 25, 1983

[54] ISOCYANURATE PREPARATION BY CATALYTIC, AMINOSILYL INITIATED CYCLOTRIMERIZATION OF ISOCYANATES

[75] Inventor: Jean Robin, Lyons, France

[73] Assignee: Rhone-Poulenc Specialites Chimiques, Courbevoie, France

[21] Appl. No.: 344,797

[22] Filed: Feb. 1, 1982

[30] Foreign Application Priority Data

Feb. 3, 1981 [FR] France .................... 81 02192
Dec. 9, 1981 [FR] France .................... 81 23135

[51] Int. Cl.³ .................... C07D 251/34; C08G 18/02; C08F 4/16
[52] U.S. Cl. .................... 544/193; 544/222; 521/128; 521/902; 528/52; 526/194
[58] Field of Search .................... 544/193, 222; 521/128; 521/902; 528/52; 526/194

[56] References Cited

PUBLICATIONS

Itoh et al., *J. Chem. Soc.* (C), pp. 2002–2009 (1969).
Saunders and Frisch, "Polyurethanes", pp. 64–65, Interscience Pub. (1962), New York.

*Primary Examiner*—John M. Ford
*Attorney, Agent, or Firm*—Burns, Doane, Swecker & Mathis

[57] ABSTRACT

Monomeric or polymeric isocyanurates, e.g., polyisocyanate/polyisocyanurates, are prepared by catalytically cyclotrimerizing an isocyanate, e.g., an aliphatic or cycloaliphatic isocyanate, in the presence of an aminosilyl catalysis initiator, e.g., a mono- or diaminosilane, a silylurea or a silazane, having the structural formula:

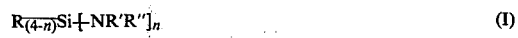

(I)

wherein R is a saturated or unsaturated, aliphatic, cycloaliphatic, aryl, aralkyl or alkylaryl monovalent hydrocarbon radical, or halo or cyano substituted such radical, and further wherein any two radicals R may together form a single divalent such hydrocarbon radical; R' is R, SiR$_3$ or an amido radical having the structural formula:

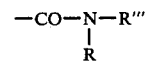

wherein R''' is R or SiR$_3$, with R being as above defined, and further wherein R', when R' is neither the amido radical nor SiR$_3$, may, together with the radical R'', form a single divalent such radical; R'' is R, or a hydrogen atom when R' is not the amido radical; and n is either 1 or 2, but when n is 2, R' is R.

20 Claims, No Drawings

ISOCYANURATE PREPARATION BY CATALYTIC, AMINOSILYL INITIATED CYCLOTRIMERIZATION OF ISOCYANATES

BACKGROUND OF THE INVENTION

1. Field of the Invention

The present invention relates to the preparation of compounds containing isocyanurate groups by the catalytic cyclotrimerization of monoisocyanates or polyisocyanates, and, more especially, to such process wherein the catalysis is initiated by contacting the isocyanate with an aminosilyl compound, such as an aminosilane, a silylurea compound or a silazane compound.

2. Description of the Prior Art

Numerous processes are known to this art for the preparation of simple or polymeric compounds containing isocyanurate groups by the catalytic cyclotrimerization of aliphatic, cycloaliphatic or aromatic isocyanates. The cyclotrimerization reaction can be either complete or partial. Thus, monoisocyanurates can be obtained from monoisocyanates, while polyisocyanate/polyisocyanurates will be prepared from polyisocyanates by partial cyclotrimerization, and polyisocyanurates devoid of free isocyanate groups will be prepared from polyisocyanates by total, or complete cyclotrimerization. Polyisocyanurates without free isocyanate groups constitute a class of polymeric materials very frequently used in cellular form (polyisocyanurate foams).

As regards the preparation of isocyanurate or polyisocyanurate by the total trimerization of aliphatic, cycloaliphatic or aromatic monoisocyanates or polyisocyanates, the following compounds are exemplary catalysts therefor: tertiary amines, phosphines, alcoholates, and alkali metal or alkaline earth metal derivatives, such as their oxides, their hydroxides, their carboxylates, and the like. These catalysts are described, for example, in *Journal of Cellular Plastics*, pp. 85–90 (January, 1965), and *Journal Macromolecular Science Reviews; Macromolecular Chemistry* (5/1), 105–109 (1970). Certain silicon and tin derivatives have also been described as catalysts for the cyclotrimerization of phenyl isocyanate to provide isocyanurate. Thus, Itoh, Matsuzaki and Ishii demonstrated the catalytic role of bis-trimethylsilyl sulfide [*Journal Chemical Society* (C), pp. 2,709–2,712 (1981)] and N-silylamines [*Journal Chemical Society* (C), pp. 2,005–2,007 (1969)]. It will be noted that the trimethylsilylamines make it possible to cyclotrimerize isocyanatobenzene very slowly to yield isocyanurate (experiments carried out for 42 hours at 150° C.). Silylamines, therefore, appear to be cyclotrimerization catalysts displaying very little activity for aromatic isocyanates. Furthermore, the above-mentioned authors also demonstrated that disilazanes (hexamethyldisilazane, heptamethyldisilazane and hexamethyl-N-ethyldisilazane) were not catalysts for the cyclotrimerization of phenyl isocyanate to yield triphenyl isocyanurate: to the contrary, these silazanes proved to be reagents which led, with phenyl isocyanate, to iminotriphenyl-hexahydrotriazine-diones [for example, 4-methylimino-1,3,5-triphenyl-hexahydro-1,3,4-triazine-2,6-dione and 1,3,5-triphenyl-2,4,6-tris-(phenylimino)hexahydro-1,3,5-triazine are obtained from heptamethyldisilazane].

Polyisocyanate/polyisocyanurates, which are base constituents for varnishes and paints, are typically obtained by the partial cyclotrimerization of the NCO groups of simple aliphatic or aromatic polyisocyanates, or of polyisocyanate adducts, with the aid of a variety of catalysts, such as tertiary amines [German Pat. No. 951,168], alkali metal or alkaline earth metal derivatives, such as hydroxides, carbonates and alcoholates [French Pat. No. 1,190,065], quaternary ammonium hydroxides [French Pat. Nos. 1,204,697 and 1,566,256 and published European Patent Application Nos. 00/03,765 and 10,589], phosphines [French Pat. Nos. 1,510,342 and 2,023,423 and published German Patent Application No. 1,934,763], catalysts containing an ethyleneimine group [French Pat. Nos. 1,401,513 and 2,230,642] and finally Mannich bases [French Pat. Nos. 2,290,459 and 2,332,274]. If appropriate, these various catalysts can also be associated with a carbamic acid ester [tertiary amine+carbamate: French Pat. No. 1,172,576; alkali metal or alkaline earth metal derivatives+carbamate: French Pat. No. 1,304,301; or Mannich base+carbamate: French Pat. No. 2,290,459].

The catalyst for the partial cyclotrimerization of the NCO groups must typically be deactivated when the desired proportion of free isocyanate groups has been reached. This deactivation can be effected by adding to the reaction mass an acid compound (a hydracid, an acid chloride or the like), an alkylating agent (methyl iodide or the like) or an acylating agent. Finally, the deactivation can be carried out by means of a suitable heat treatment.

Thus, various catalyst systems were known which made it possible to trimerize aliphatic or cycloaliphatic isocyanates to provide isocyanurate compounds (simple isocyanurates or polyisocyanate/polyisocyanurates), but these various systems are all characterized by one or more serious disadvantages. Catalysis by alkali metal and alkaline earth metal derivatives, for example, always takes place unpredictably, with a certain time delay, and is then sudden and generally difficult to control because of its excessively high activity. With less reactive catalyst systems, the delay in the catalytic activity is no longer observed, but the catalysis is relatively ineffective. It is necessary to cyclotrimerize at a high temperature, and this causes the formation of a considerable amount of dimer. Furthermore, it is generally necessary to heat during the period of deactivation of the catalyst, and this also favors the formation of dimer.

Serious need therefore exists in the art for a catalyst system which make it possible to cyclotrimerize aliphatic or cycloaliphatic isocyanates to give compounds containing isocyanurate groups, the catalytic reaction taking place without an induction period and in a uniform manner at a relatively moderate temperature. It is furthermore important for any catalyst of such desired type to be readily deactivated.

SUMMARY OF THE INVENTION

Accordingly, a major object of the present invention is the provision of an improved process for the preparation of monomeric or polymeric compounds comprising isocyanurate groups, which process being conspicuously devoid of those disadvantages and drawbacks to date characterizing the state of the art, while at the same time providing all of those desiderata immediately above outlined, and which process featuring the catalytic cyclotrimerization of isocyanates in which the isocyanate group is not directly bonded to an aromatic carbon atom, said cyclotrimerization being carried out by contacting the isocyanate with a compound which initiates the catalytic reaction, said catalytic reaction initiating compound being a compound comprising an aminosilyl function and having the structural formula (I):

$R_{(4-n)}Si—[NR'R'']_n$      (I)

in which the various symbols respectively represent the following:

R: a monovalent hydrocarbon radical, which is saturated or unsaturated aliphatic or cycloaliphatic, aryl, aralkyl or alkylaryl, optionally substituted by halogen atoms or CN groups, it also being possible for any two radicals R to together form a single divalent hydrocarbon radical;

R': a monovalent radical selected from among the radicals R, SiR$_3$ or the amide radicals having the formula:

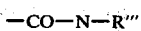

$$-CO-N-R'''$$
$$\quad\quad\;\;|$$
$$\quad\quad\;\;R$$

with R''' representing R or SiR$_3$, and R having the meaning given above, it being possible, if appropriate, for the radical R' to form a divalent hydrocarbon radical with the radical R'', if it does not represent an amide group or a group SiR$_3$;

R'': a monovalent radical having the same meaning as the radical R, or a hydrogen atom if R' is not an amide radical; and n: an integer equal to 1 or 2; if n is equal to 2, R' is a radical R.

DETAILED DESCRIPTION OF THE INVENTION

More particularly according to this invention, the cyclotrimerization initiating compound, to provide the isocyanurate, and which will hereinafter be designated more conveniently by the term catalyst, has now been demonstrated to be unexpectedly particularly valuable for the cyclotrimerization of the aliphatic or cycloaliphatic isocyanates. The catalyst, which can be an aminosilane, a diaminosilane, a silylurea or a silazane, is remarkable in that its catalytic action is immediate, uniform and rapid at moderate temperature. A result of this type is indeed unexpected. In fact, in view of the lower reactivity which aliphatic isocyanates usually exhibit compared with aromatic isocyanates [compare, for example, *Polyurethanes, Chemistry and Technology*, part I, Chemistry, page 64, by J. H. Saunders and K. C. Frisch, Interscience Publishers (1962)], it was to be expected that a greatly reduced catalytic activity would be obtained, since a very low catalytic activity is observed with aromatic isocyanates. Nonetheless, just the opposite effect has been realized by the present invention.

Furthermore, when using silazanes as catalysts, isocyanurates are obtained in the aliphatic or cycloaliphatic isocyanate series, as already above mentioned. This result is totally unexpected since Itoh et al, supra, have reported that iminohexahydrotriazines were obtained in the aromatic isocyanate series.

More preferably, the present invention relates to a process for the preparation of compounds containing isocyanurate groups by catalysis with compounds containing aminosilyl groups and having the structural formula (I), in which the various symbols respectively represent the following:

R: an alkyl, alkenyl, halogenoalkyl or halogenoalkenyl radical having from 1 to 5 carbon atoms and containing from 1 to 6 chlorine and/or fluorine atoms, cycloalkyl, cycloalkenyl, halogenocycloalkyl and halogenocycloalkenyl radicals having from 3 to 8 carbon atoms and containing from 1 to 4 chlorine and/or fluorine atoms, aryl, alkylaryl and halogenoaryl radicals having from 6 to 8 carbon atoms and containing from 1 to 4 chlorine and/or fluorine atoms, or cyanoalkyl radicals having from 3 to 4 carbon atoms, and further wherein any two substituents R borne by one and the same silicon atom may together form a single divalent hydrocarbon radical having from 1 to 4 carbon atoms;

R': a monovalent radical selected from among R, SiR$_3$ and CO(NR)—R''' radicals, R''' representing R or SiR$_3$, and R having the more precise meaning defined above, it also being possible for R' to form, with R, a single alkylene radical having from 4 to 6 carbon atoms; and R'': an alkyl or alkenyl radical having from 1 to 4 carbon atoms, a cycloalkyl or cycloalkenyl radical having from 4 to 6 nuclear carbon atoms, a phenyl, tolyl or xylyl radical, or a hydrogen atom if R' is not an amide group.

By way of illustration, the following are representative of the aforesaid substituents:

for R: methyl groups, ethyl groups, propyl groups, isopropyl groups, butyl groups, isobutyl groups, α-pentyl groups, t-butyl groups, chloromethyl groups, dichloromethyl groups, α-chloroethyl groups, α,β-dichloroethyl groups, fluoromethyl groups, difluoromethyl groups, α,β-difluoroethyl groups, 3,3,3-trifluoropropyl groups, trifluorocyclopropyl groups, 4,4,4-trifluorobutyl groups, 3,3,3,4,4,5,5-heptafluoropentyl groups, β-cyanoethyl groups, γ-cyanopropyl groups, phenyl groups, p-chlorophenyl groups, m-chlorophenyl groups, 3,5-dichlorophenyl groups, trichlorophenyl groups, tetrachlorophenyl groups, o-, p- or m-tolyl groups, α,α,α-trifluorotolyl groups and xylyl groups (2,3-dimethylphenyl and 3,4-dimethylphenyl), and further wherein any two radicals R may together form a methylene, ethylene or propylene radical;

for R': a radical R or SiR$_3$ wherein R is immediately above defined, or a radical —CO—(NR)—R''', R''' representing R or SiR$_3$, and R also being as immediately above defined, with the proviso that R', together with R'', may also form a butylene, pentylene or hexylene radical;

for R'': hydrogen, methyl groups, butyl groups, cyclohexyl groups, phenyl groups and tolyl groups.

Most preferably, the present invention relates to a process for the preparation of compounds containing isocyanurate groups by catalysts with aminosilyl compounds having the structural formula (I), in which the various symbols respectively represent the following:

R: a methyl, ethyl, propyl, vinyl or phenyl radical, it being possible, if appropriate, for these radicals to be chlorinated and/or fluorinated;

R': an alkyl radical selected from among methyl, ethyl, propyl or butyl radicals, a radical SiR$_3$, R being as immediately above defined, or a carbonamide radical selected from among: CO—NR—R and —CO—NR—SiR$_3$, R again being as immediately above defined; and R″0 a methyl, ethyl, propyl or butyl radical, or a hydrogen atom.

Finally, R′ and R″ can together form a butylene or pentylene radical.

As hereinbefore noted, the catalyst can be an aminosilane, a diaminosilane, a monosilylurea, a disilylurea or a silazane. The various compounds containing aminosilyl groups contemplated herein are thus readily determined, in view of the aforesaid definitions of the various radicals R, R′, R″ and R‴. It will be noted, in particular, that the use of a silylurea obtained by reacting a secondary amine with N-silyl isocyanates is not envisaged. These silylureas are unsuitable in the process of the invention because they release the silyl isocyanate upon heating.

The processes consistent herewith for the preparation of monomeric or polymeric compounds containing isocyanurate groups by the catalytic cyclotrimerization of isocyanates in which the isocyanate group is not directly bonded to an aromatic carbon atom, and which employ, as the catalyst:

(i) A monoaminosilane (n being equal to 1, R′ representing a radical R, and the radicals R and R″ being as above defined, and it being possible for two radicals R to together form a divalent radical or alternatively for R′ and R″ to together form a divalent radical);

(ii) a diaminosilane (n being equal to 2; R′ representing a radical R, and the radicals R and R″ being as above defined, or it also being possible for two radicals R to together form a divalent radical or for two radicals R′ and R″ to together form a divalent radical);

(iii) A silylurea (n being equal to 1 and R′ representing a carbonamide radical

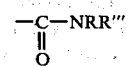

in which R‴ represents a radical R or SiR$_3$, the radicals R and R″ being as above defined, and it also being possible for two radicals R to together form a divalent radical or for the two radicals R′ and R‴ (R′ then representing R) to together form a divalent radical); or (iv) A silazane (n being equal to 1 and R′ representing a group SiR$_3$); obviously constitute more specific embodiments of the present invention.

The following are exemplary of the aminosilanes or diaminosilanes: methylamino-trimethylsilane, dimethylamino-trimethylsilane, diethylamino-trimethylsilane, dibutylamino-trimethylsilane, diethylamino-dimethyl-vinylsilane, diethylamino-dimethyl-phenylsilane, bis-dimethylamino-dimethylsilane, bis-diethylamino-dimethylsilane, bis-dibutylamino-dimethylsilane and bis-dimethylamino-methyl-phenylsilane.

The following are exemplary of the silylureas: N-methyl-N-trimethylsilyl-N′-methyl-N′-butylurea, N-trimethylsilyl-N-methyl-N′,N′-dimethylurea, N-trimethylsilyl-N-ethyl-N′,N′-dimethylurea and N-trimethylsilyl-N-butyl-N′-butyl-N′-trimethylsilylurea.

The silazanes can be symmetrical or asymmetrical; as a preferred embodiment of the present invention, it is preferred to use symmetrical disilazanes, with the two SiR$_3$ groups being identical.

The following are exemplary of the disilazanes which are envisaged: hexamethyldisilazane, heptamethyldisilazane, 1,3-diethyl-1,1,3,3-tetramethyldisilazane, 1,3-divinyl-1,1,3,3-tetramethyldisilazane, hexaethyldisilazane and 1,3-diphenyl-1,1,3,3-tetramethyldisilazane.

Finally, hexamethyldisilazane and heptamethyldisilazane, which prove to be very particularly advantageous catalysts, are the more preferred from among the disilazanes.

The process according to the invention enables one to cyclotrimerize "simple" monoisocyanates or polyisocyanates of aliphatic or cycloaliphatic type, and also polyisocyanate adducts (resulting from the polycondensation of excess polyisocyanate with a polyfunctional compound). The cyclotrimerization reaction can be either partial or total: same enables obtainment of, starting from monoisocyanates, compounds containing a single isocyanurate group, such as alkyl or cycloalkyl isocyanurates, and, starting from simple polyisocyanates or polyisocyanate adducts, polyisocyanate/polyisocyanurates and also polyisocyanurates having a very high molecular weight and devoid of free isocyanate groups.

Any simple isocyanate or polyisocyanate of aliphatic or cycloaliphatic type, or any isocyanate adduct or prepolymer, is suitable, provided, as already stated, that the isocyanate group is not directly bonded to an aromatic carbon.

The following monoisocyanates are representative of the isocyanates which are intended: methyl isocyanate, butyl isocyanate, n-hexyl isocyanate and cyclohexyl isocyanate.

The following are representative of the diisocyanates which are intended: tetramethylene diisocyanate, pentamethylene diisocyanate, hexamethylene diisocyanate, 1,2-diisocyanatocyclohexane, 1,4-diisocyanatocyclohexane, 1,2-bis-(isocyantomethyl)-cyclobutane, bis-(4-isocyanatocyclohexyl)-methane and 3,3,5-trimethyl-5-isocyanatomethyl-1-isocyantocyclohexane.

From among the aforesaid compounds, hexamethylene diisocyanate is especially advantageous.

Finally, among the polyisocyanate adducts or prepolymers which are intended, exemplary are the modified polyisocyanates which are obtained by reacting excess aliphatic or cycloaliphatic polyisocyanate with a compound containing at least two groups which are reactive with isocyanate groups, such as a diamine, a diacid, or the like. The modified polyisocyanates, which can be mixed with simple polyisocyanates, can contain urea groups, biuret groups, ester groups, siloxane groups, or the like.

Although the order of introduction of the reactants is not critical, the process according to the invention is advantageously carried out by introducing a small amount of the catalyst into the isocyanate; this amount, expressed by weight relative to the isocyanate employed, normally ranges from about 0.1 to 10% and preferably from about 0.5 to 5%. If appropriate, additional small amounts of catalyst can be introduced during the reaction itself.

The process is carried out by simply heating the reactants to a temperature which typically ranges from 50° to 180° C. and preferably from 80° to 130° C.

When the proportion of isocyanurate attains the desired value, the catalyst can be destroyed, for example, by adding an acid compound (a strong acid, such as hydrochloric acid, an acid chloride, or the like). A process of this type, which makes it possible to obtain polyisocyanate/polyisocyanurates, circumscribes another embodiment of the present invention.

It is then possible, if appropriate, to remove the monomeric polyisocyanate by any known means and to obtain a polyisocyanate/polyisocyanurate containing an excessively reduced proportion of monomeric isocyanate and also a small proportion of dimer. Compounds of this type, such as those derived from hexamethylene diisocyanate, are well-known compounds which are particularly valuable as base constituents for varnishes and paints.

It is also possible, if necessary, to carry out the cyclotrimerization reaction in a solvent reaction medium, it being possible for the latter to be a solvent of low polarity, such as, for example, an aliphatic or aromatic hydrocarbon, an ester or an ether, and it is then possible to introduce the catalyst into the solvent and to introduce the isocyanate into this solution. Obviously, it is also possible to introduce the catalyst solution into the isocyanate. Advantageously, the subject process is carried out in the absence of any solvent.

In order to further illustrate the present invention and the advantages thereof, the following specific examples are given, it being understood that same are intended only as illustrative and in nowise limitative.

EXAMPLE 1

The following material was introduced into a round-bottomed flask:

(i) Butyl isocyanate: 39.6 g (namely 0.4 mol) and the following was then added thereto:

(ii) N,N-dimethyl-trimethylsilylamine: 4.7 g (namely, 0.04 mol).

The mixture was next heated in an oil bath to an internal temperature of 100°–105° C.; after 14 hours at 100°–110° C., 90% of the NCO groups present had been consumed.

Distillation yielded 20.8 g of a product boiling at 142° C. under 1 mm of mercury and identified as being tributyl isocyanurate:

C% = 60.4 (theory 60.6)
H% = 9.14 (theory 9.1)
N% = 14.5 (theory 14.15)
$n_D^{20} = 1.474$ Infra-red absorption: at 1,460 cm$^{-1}$ and 1,690 cm$^{-1}$

EXAMPLE 2

The procedure of Example 1 was repeated, except that the N,N-dimethyl-trimethylsilylamine was replaced with 5.8 g of N,N-diethyl-trimethylsilylamine (0.04 mol).

After 17 hours at 100°–110° C., 88% of the NCO groups present had been consumed. 20.8 g of tributylisocyanurate, defined as above, were separated by distillation.

C% = 60.82 (theory 60.6)
H% = 9.17 (theory 9.1)
N% = 14.03 (theory 14.15)

EXAMPLE 3

The following material was introduced into a round-bottomed flask:

(i) Hexamethylene diisocyanate: 537.6 g (namely, 3.2 mols).

Same was heated to 100° C. and the following was introduced into the isocyanate:

(ii) N,N-Dimethyl-trimethylsilylamine: 7.5 g (0.063 mol).

After 1 hour, 30 minutes, at 100° C., 15% of the NCO groups present had been consumed. The reaction was terminated by adding 7 ml of benzoyl chloride. The major fraction of the residual hexamethylene diisocyanate was distilled up to 130° under 1.5 mm.

184 g of product then remained, and this was distilled in an agitated thin-film evaporator. This yielded 103 g of cyclotrimer containing 0.546 NCO/100 g (theory for the hexamethylene diisocyanate trimer: 0.595) and having a viscosity of 16 poises at 25° C.

EXAMPLE 4

The following materials were introduced into a round-bottomed flask:

(i) Butyl isocyanate: 29.7 g (0.3 mol); and
(ii) Bis-(dimethylamino)-dimethylsilane: 0.88 g (0.006 mol).

The mixture was heated in an oil bath to an internal temperature of 105° C.; after 14 hours at 105° C., 88% of the NCO groups present had been consumed.

Distillation under a pressure of 0.5 mm of mercury yielded 17.9 g of product passing over at 132°–134° C. and identified as being tributyl isocyanurate.

EXAMPLE 5

As in Example 4, a mixture consisting of:

(i) Butyl isocyanate: 29.7 g (0.3 mol); and
(ii) Trimethylsilylbutylamine: 0.87 g was heated to 105° C.

After 23 hours at 105° C., 67% of the NCO groups had disappeared.

Distillation under a pressure of 0.5 mm of mercury yielded 15.7 g of product boiling at between 132° and 135° C. and identified as being tributyl isocyanurate.

EXAMPLE 6

29.7 g (0.3 mol) of butyl isocyanate were introduced into a round-bottomed flask and 1.45 g of hexamethyldisilazane (0.03 mol) were then charged therein, at ambient temperature, over the course of 10 minutes. The mixture was heated at 100° for 2 hours and then at 110°. After a reaction time of 16 hours, there remained only 7% of the initial isocyanate groups.

The reaction mixture was distilled and 2.35 g of volatile products were separated off; the residue, 13.35 g, was tributyl isocyanurate, characterized by the IR absorption bands at 1,465 and 1,690 cm$^{-1}$ (no urea, biuret or carbodiimide band was detected). The microanalysis was consistent with theory.

|     | determined |       | theory |
| --- | --- | --- | --- |
| C % | 60.76 | 61.04 | 60.6 |
| H % | 9.1 | 9.48 | 9.1 |
| N % | 14.06 | 14.16 | 14.15 |

EXAMPLE 7

An experiment analogous to that described in Example 6 was carried out, but with 2 mols of hexamethyldisilazane per 100 mols of butyl isocyanate. After the reaction, there remained only 10% of the original isocyanate groups.

The distilled product provided 20.75 g of tributyl isocyanurate (boiling point (0.2 mm of mercury): 125°; melting point: 9°–10°; $n_D^{20} = 1.4750$).

It was thus found that one mol of hexamethyldisilazane effected the disappearance of 90 mols of butyl isocyanate.

EXAMPLE 8

134.8 g of hexamethylene diisocyanate (0.8 mol) and 1.3 g of hexamethyldisilazane (0.008 mol) were introduced into a round-bottomed flask and the mixture was then heated at 100° for 7 hours. The proportion of NCO groups was then 1.07 groups per 100 g.

The excess hexamethylene diisocyanate was distilled and the residue was then transferred into an agitated thin-film evaporator. This yielded 19 g of product containing 0.55 NCO/100 g (theory for tris-(isocyanato-hexamethylene) isocyanurate: 0.59).

In The IR spectrum, this product evidenced the bands characteristic of the isocyanurate trimer (1,645 and 1,690 cm$^{-1}$) and the NCO band at 2,270 cm$^{-1}$. Its viscosity was 25 poises at 25° C. and its fingerprint gas-phase chromatogram evidenced that it was essentially composed of trimer of molecular weight 504. The proportion of dimer was less than 5%. The proportion of free hexamethylene diisocyanate was less than 0.1%.

EXAMPLE 9

The following materials were introduced into a 100 ml three-necked round-bottomed flask with a magnetic stirrer, a reflux condenser and a nitrogen inlet:

(i) Butyl isocyanate: 24.75 g (0.25 mol); and
(ii) Heptamethyldisilazane: 4.4 g (0.025 mol), heating being provided by an oil bath.

The mixture was heated to 100°–110°. After 3 hours, half of the NCO groups present had been consumed. After a reaction time of 16 hours, there remained only 8% of the original NCO groups, i.e., a consumption of 9.2 mols of butyl isocyanate per mol of heptamethyldisilazane.

Distillation of the residual reaction mixture (22.2 g) provided 14.45 g of product passing over at 112°–132° under 0.1 to 0.25 mm. This product was tributyl isocyanurate ($n_D^{20}$=1.4760; IR spectrum consistent).

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of a monomeric or polymeric isocyanurate compound, comprising catalytically cyclotrimerizing an isocyanate in which the isocyanate moiety is not directly bonded to an aromatic carbon atom, in the presence of an effective amount of an aminosilyl catalysis initiator having the structural formula:

 (I)

wherein R is a saturated or unsaturated, aliphatic, cycloaliphatic, aryl, aralkyl or alkylaryl monovalent hydrocarbon radical, or halo or cyano substituted such radical, and further wherein any two radicals R may together form a single divalent such hydrocarbon radical; R' is R, SiR$_3$ or an amido radical having the structural formula:

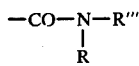

wherein R''' is R or SiR$_3$, with R being as above defined, and further wherein R', when R' is neither the amido radical nor SiR$_3$, may, together with the radical R'', form a single divalent such radical; R'' is R, or a hydrogen atom when R' is not the amido radical; and n is either 1 or 2, but when n is 2, R' is R.

2. The process as defined by claim 1, said aminosilyl catalysis initiator being a monoaminosilane.

3. The process as defined by claim 1, said aminosilyl catalysis initiator being a diaminosilane.

4. The process as defined by claim 1, said aminosilyl catalysis initiator being a silylurea.

5. The process as defined by claim 1, said aminosilyl catalysis initiator being a silazane.

6. The process as defined by claim 1, said isocyanate starting material being an aliphatic isocyanate.

7. The process as defined by claim 1, said isocyanate starting material being a cycloaliphatic isocyanate.

8. The process as defined by claim 1, wherein the aminosilyl catalysis initiator having the structural formula (I), R is an alkyl, alkenyl, halogenoalkyl or halogenoalkenyl radical having from 1 to 5 carbon atoms and containing from 1 to 6 chlorine and/or fluorine atoms, a cycloalkyl, cycloalkenyl, halogenocycloalkyl or halogenocycloalkenyl radical having from 3 to 8 carbon atoms and containing from 1 to 4 chlorine and/or fluorine atoms, an aryl, alkylaryl or halogenoaryl radical having from 6 to 8 carbon atoms and containing from 1 to 4 chlorine and/or fluorine atoms, or a cyanoalkyl radical having from 3 to 4 carbon atoms, and further wherein any two substituents R borne by one and the same silicon atom may together from a single divalent hydrocarbon radical having 1 to 4 carbon atoms; R' is R, SiR$_3$ or CO(NR)—R''', wherein R''' is R or SiR$_3$, with R being as above defined, and further wherein R' may, together with R, form a single alkylene radical having from 4 to 6 carbon atoms; and R'' is an alkyl or alkenyl radical having from 1 to 4 carbon atoms, a cycloalkyl or cycloalkenyl radical having from 4 to 6 nuclear carbon atoms, a phenyl, tolyl or xylyl radical, or a hydrogen atom if R' is not an amido radical.

9. The process as defined by claim 1, wherein the aminosilyl catalysis initiator having the structural formula (I), R is methyl, ethyl, propyl, isopropyl, butyl, isobutyl, α-pentyl, t-butyl, chloromethyl, dichloromethyl, α-chloroethyl, α,β-dichloroethyl, fluoromethyl, difluoromethyl, α,β-difluoroethyl, 3,3,3-trifluoropropyl, trifluorocyclopropyl, 4,4,4-trifluorobutyl, 3,3,3,4,4,5,5-heptafluoropentyl, β-cyanoethyl, γ-cyanopropyl, phenyl, p-chlorophenyl, m-chlorophenyl, 3,5-dichlorophenyl, trichlorophenyl, tetrachlorophenyl, o-, p- or m-tolyl, α,α,α-trifluorotolyl, 2,3-dimethylphenyl or 3,4-dimethylphenyl, and further wherein any two radicals R may together form a methylene, ethylene or propylene radical; R' is R, SiR$_3$ or —CO—(NR)—R''', with R being as above defined, and wherein R''' is R or SiR$_3$, with R also being as above defined, and further wherein R' may, together with R'', form a butylene, pentylene or hexylene radical; and R'' is hydrogen, methyl, butyl, cyclohexyl, phenyl or tolyl.

10. The process as defined by claim 1, wherein the aminosilyl catalysis initiator having the structural formula (I), R is methyl, ethyl, propyl, vinyl or phenyl, or chlorinated and/or fluorinated such radicals; R' is methyl, ethyl, propyl, butyl, SiR$_3$, —CO—NR—R or —CO—NR—SiR$_3$, with R being as above defined; and R'' is methyl, ethyl, propyl, butyl or hydrogen; and further wherein R' may, together with R'', form a butylene or pentylene radical.

11. The process as defined by any of claims 1, 8, 9 or 10, said aminosilyl catalysis initiator having the structural formula:

$R_3SiNR'R''$.

12. The process as defined by any of claims 1, 8, 9 or 10, said aminosilyl catalysis initiator having the structural formula:

$R_2Si(NR'R'')_2$.

13. The process as defined by any of claims 1, 8, 9 or 10, said aminosilyl catalysis initiator having the structural formula:

$$R_3Si-\underset{R''}{N}-\underset{\|}{\overset{O}{C}}-\underset{R}{N}-R'''.$$

14. The process as defined by any of claims 1, 8, 9 or 10, said aminosilyl catalysis initiator having the structural formula:

$$R_3Si-\underset{R''}{N}-SiR_3.$$

15. The process as defined by claim 1, for the preparation of a polyisocyanate/polyisocyanurate by catalytically cyclotrimerizing an aliphtic or cycloaliphatic polyisocyanate, or polyisocyanate adduct or prepolymer thereof, and comprising destruction of the catalysis initiator when the degree of isocyanurate formation has attained the desired level.

16. The process as defined by claim 15, said catalysis initiator destruction being effected by addition of an acid compound to the reaction medium.

17. The process as defined by claims 15 or 16, further comprising removal of residual polyisocyanate upon completion of the reaction.

18. The process as defined by claim 1, said isocyanate catalytically cyclotrimerized being hexamethylene diisocyanate.

19. The process as defined by claim 1, said aminosilyl catalysis initiator being methylamino-trimethylsilane, dimethylamino-trimethylsilane, diethylamino-trimethylsilane, dibutylamino-trimethylsilane, diethylamino-dimethyl-vinylsilane, diethylamino-dimethyl-phenylsilane, bis-dimethylamino-dimethylsilane, bis-diethylamino-dimethylsilane, bis-dibutylamino-dimethylsilane, bis-dimethylamino-methyl-phenylsilane, N-methyl-N-trimethylsilyl-N'-methyl-N'-butylurea, N-trimethylsilyl-N-methyl-N',N'-dimethylurea, N-trimethylsilyl-N-ethyl-N',N'-dimethylurea, N-trimethylsilyl-N-butyl-N'-butyl-N'-trimethylsilylurea, hexamethyldisilazane, heptamethyldisilazane, 1,3-diethyl-1,1,3,3-tetramethyldisilazane, 1,3-divinyl-1,1,3,3,-tetramethyldisilazane, hexaethyldisilazane or 1,3-diphenyl-1,1,3,3-tetramethyldisilazane.

20. The process as defined by claim 1, said isocyanate catalytically cyclotrimerized being methyl isocyanate, butyl isocyanate, n-hexyl isocyanate, cyclohexyl isocyanate, tetramethylene diisocyanate, pentamethylene diisocyanate, hexamethylene diisocyanate, 1,2-diisocyanatocyclohexane, 1,4-diisocyanatocyclohexane, 1,2-bis-(isocyanatomethyl)-cyclobutane, bis-(4-isocyantocyclohexyl)-methane or 3,3,5-trimethyl-5-isocyanatomethyl-1-isocyantocyclohexane.

* * * * *